US007896860B2

(12) United States Patent
Shimizu et al.

(10) Patent No.: US 7,896,860 B2

(45) Date of Patent: Mar. 1, 2011

(54) TRANSPORTATION DEVICE OF MEDICINE

(75) Inventors: Kaoru Shimizu, Shizuoka (JP); Yasuhiro Muramatsu, Shizuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 661 days.

(21) Appl. No.: 11/856,230

(22) Filed: Sep. 17, 2007

(65) Prior Publication Data

US 2008/0097372 A1 Apr. 24, 2008

Related U.S. Application Data

(63) Continuation of application No. PCT/JP2006/305076, filed on Mar. 15, 2006.

(30) Foreign Application Priority Data

Mar. 15, 2005 (JP) ............................ 2005-072810

(51) Int. Cl.
*A61B 19/00* (2006.01)

(52) U.S. Cl. ........................ 604/415; 604/411; 604/416

(58) Field of Classification Search ................. 604/403, 604/411, 414–416

See application file for complete search history.

(56) References Cited

U.S. PATENT DOCUMENTS 4,610,374 A 9/1986 Buehler
5,358,501 A 10/1994 Meyer
2007/0060903 A1 3/2007 Miyajima et al.
2007/0208320 A1 9/2007 Muramatsu et al.
2008/0033390 A1 2/2008 Kitagawa et al.

FOREIGN PATENT DOCUMENTS

JP 4-500331 1/1992
JP 6-59302 3/1994
WO WO 91/07160 5/1991

OTHER PUBLICATIONS

U.S. Appl. No. 12/436,172, filed May 6, 2009, Muramatsu.
U.S. Appl. No. 12/512,427, filed Jul. 30, 2009, Muramatsu.

*Primary Examiner*—Leslie R Deak
(74) *Attorney, Agent, or Firm*—Oblon, Spivak, McClelland, Maier & Neustadt, L.L.P.

(57) ABSTRACT

A container for addition (co-infusion) of medicine to an infusion bag and aims to keep a positive sealed condition while preventing a number of parts from being increased and while maintaining a positive releasing of the sealed condition when an infusion process is carried out. A breakable lug 20 is integrally formed at a end of a port body 10 to which a soft container 80 for storing therein with a co-infusion liquid under a sealed manner, which lug 20 is able to be broken in order to obtain a release function. A rubber plug 98 of an infusion bag 90 is pierced by a needle body 11, while the port body 10 is press fitted into a straight bore of the needle body 11, so that the lug 20 is contacted with an opposed bottom wall of the needle body 11, resulting in at least partial breakage of the lug 20, thereby forming an opening 89 at the portion where the breakage is taken place, so that the medicine in the soft container 80 is transported (co-infused) into the infusion bag 90.

16 Claims, 8 Drawing Sheets

TRANSPORTATION DEVICE OF MEDICINE

TECHNICAL FIELD

The present invention relates to a transportation device of a medicine, which is suitable for a medical operation, such as an addition of a medicine (co-infusion) to a medical bag, such as a dripping bag during an execution of an infusion operation.

BACKGROUND TECHNOLOGY

When an infusion operation such as a dripping infusion is done from a medical bag (first medical storage) for storing therein with medicines (first medicines) such as a liquid glucose and physiological saline, et al, a situation may occur that an addition (co-infusion) of different medicines (second medicines) such as vitamins to the medical bag is needed. Such a medical bag for infusion is formed as a bag from a flexible plastic film such as polyethylene, the medical bag having a sealed structure of an outlet port, which is provided with a plug made of an elastic material such as a rubber (first rubber plug). A co-infusion container (second medical storage) for storing therein with medicines for co-infusing operation with the medical bag is formed as a rigid plastic mold body and is provided with a rubber plug (second rubber plug) for sealing an injection port (co-infusion port) of a needle shape. Under un-wrapped condition of the second rubber plug, the needle shaped injection port of the second medical storage pierces the first rubber plug, which causes the medicine(s) in second medical storage medicine to be introduced into the first medical storage for obtaining co-infusion operation. As a system of such a principle of transportation, a relatively movable structure of a body (cylindrical portion) of a needle shaped injection port of the second medical storage (co-infusion container) is proposed. In this structure, when the needle shaped injection port of the second medical storage (co-infusion container) pierces the first rubber plug sealing the first medical storage, the second rubber plug sealing the second medical storage is broken, which allows the co-infusion process to be commenced. See patent publication No. 1.

Patent Publication No. 1: Japanese Examined Patent Publication No. 6-59302

DISCLOSURE OF THE INVENTION

Problem to be Solved by the Invention

In the prior art, a rubber plug (second rubber plug) seals the co-infusion container (second medical storage). Upon a piercing of a rubber plug (first rubber plug) of the first medical storage by the needle shaped injection port of the co-infusion container, a relative movement of the body of the needle shaped injection port is generated. Due to such a relative movement, the second rubber plug is opened, so that a transportation (co-infusion) of the second medicine in the co-infusion container to the first medical storage is occurred. In this prior art, the second rubber plug for obtaining a sealed structure of the co-infusion container is press fitted to the latter in a manner that a relative movement for separating the second rubber plug is generated when commencing a co-infusion process. However, such a press fitting makes the structure to be complicated on one hand and, on the other hand, a number of parts to be increased, resulting in a problem of an increased production cost. Furthermore, it may be likely that the rubber plug is completely separated and is dropped to the space inside the co-infusion container. In order to prevent such a separation from being occurred, an improvement of a rubber plug supported by a flexible member has been proposed, which, however, makes the structure to be highly completed.

The present invention aims to overcome the above-mentioned problems in the prior art and to provide a structure by which a positive sealing function is obtained during a transportation (co-infusion) process without increasing number of parts.

Means for Solving the Problem

According to the invention claimed in claim 1, a medical transportation device is provided, which comprises: a first body for receiving a medicine from a storage thereof, and; a second body connected relatively movably with the first body and having an opening for discharging the medicine at a position spaced from the fist body; the medicine being normally under a sealed condition with respect to said opening; said first and second bodies having, in the direction of said relative movement, opposed areas, which are at least partially broken during said relative movement for releasing said sealed condition, thereby allowing the transportation of the medicine from said opening.

According to the invention claimed in claim 2, a medical transportation device according to claim 1 is provided, wherein said at least partially broken part during said relative movement is a weak part, which is integrally formed to the rest.

According to the invention claimed in claim 3, a medical transportation device is provided, which comprises: a first cylindrical body for receiving a medicine from a storage thereof, and; a second cylindrical body slidably movably inserted to the first cylindrical body and having an opening for discharging the medicine at a position spaced from the fist body; said first and second cylindrical bodies having first and second ends, respectively, which are opposite in the direction of said slide movement; the medicine being normally under a sealed condition in said first cylindrical body; a relative slide movement between the first and second cylindrical bodies causing said opposed ends to be contacted with each other, so that a part of the first end contacting the second end is at least partially broken, resulting in a release of the sealed condition of the medicine in the first cylindrical body, thereby allowing the medicine to be transported from said opening.

According to the invention claimed in claim 4, a medical transportation device is provided, which is for transporting, to a first medicine sealed in a first storage by a plug made of an elastic material, a second medicine in a second storage, said device comprising: a first cylindrical body opened to the second storage for receiving the medicine from the second storage, and; a second cylindrical body slidably movably inserted to the first cylindrical body and having a needle portion at its end remote from said first cylindrical body: said needle portion being adapted for piercing to said plug for transporting said second medicine into said first storage; said first and second cylindrical bodies having first and second ends, respectively, which are opposite in the direction of said slide movement; the second medicine being normally under a sealed condition in said first cylindrical body; a relative slide movement between the first and second cylindrical bodies causing said opposed ends to be contacted with each other, so that a part of the first end contacting the second end is at least partially broken, resulting in a release of the sealed condition of the medicine in the first body, thereby allowing the medicine to be transported from said needle portion.

According to the invention claimed in claim 5, a medical transportation device according to claim 4 is provided, wherein a value of slide resistance force between the first and second cylindrical bodies is larger than a value of piercing resistance force of said plug by said needle portion.

According to the invention claimed in claim 6, a medical a medical transportation device according to claim 3 or 4 is provided, wherein said part of the first end of the first cylindrical body broken at least partially is a lug, which extends, in cantilever fashion, toward the second end of the second cylindrical body.

According to the invention claimed in claim 7, a medical transportation device according to claim 6 is provided, wherein said lug is an integrally formed part of said first cylindrical body, and said first end is provided with a weak part connected to said lug.

According to the invention claimed in claim 8, a medical transportation device according to claim 6 or 7 is provided, wherein said second end of the second cylindrical body has a recess having a shape, which is complimentary with that of the lug at the first end of the first cylindrical member.

According to the invention claimed in claim 9, a medical transportation device according to claim 8 is provided, wherein it further comprises means for relative rotational positioning between said first and second cylindrical bodies during their relative slide movement.

According to the invention claimed in claim 10, a medical transportation device according to any one of claims 3 to 9 is provided, wherein it further comprises means for confirming a completion of said relative movement between the first and second cylindrical bodies until a release of the sealed condition by said breakage.

According to the invention claimed in claim 11, a method is provided for transportation to a first medical storage storing a first medicine under a sealed manner by a plug made of an elastic material from a second storage storing in a sealed manner a second medicine, said method comprising the steps of: providing a transportation device having first cylindrical body opened to the second storage, and a second cylindrical body slidably movably inserted to the first cylindrical body and formed as a needle having an opening at its end remote from the first cylindrical body; inserting at first the medicine in said second storage into said first cylindrical body, while being held therein under a sealed condition; piercing said needle to said plug of the first storage; moving said first and second cylindrical bodies relatively in a manner that said opposed ends in the direction of the relative movement are contacted and broken at least partially, so that said sealed condition of the second medicine in the first body is released, and; moving the second medicine into the first storage by way of said opening, so that the second medicine is mixed to the first medicine in said first storage.

According to the invention claimed in claim 12, a medical transportation device according claim 11, further comprising the step of adjusting a value of a resistance force of the slide movement between the first and second cylindrical bodies is larger than a value of resistance force as occurred when said plug is pierced by said needle portion.

Operational Effects of the Invention

In an operational effect of the invention claimed in claim 1, the medicine in the first body is inwardly sealed under a usual condition, which prevents the medicine from being discharged from the opening. A discharge of the medicine is obtained by a relative movement between the first and second bodies, by which relative movement the opposed areas are at least partially broken, resulting in a release of the inner sealed condition of the medicine and in a discharge of the medicine by way of the opening. Thanks to the release of the medicine by the breakage of the opposed areas, a separate part otherwise needed, such as a rubber plug, is eliminated, resulting in a corresponding reduction in cost, while obtaining a simplified and positive opening operation.

In an operational effect of the invention claimed in claim 2, the integrated structure of the partial breakable part assures a further reduction in the cost, while keeping a reliable release operation.

In an operational effect of the invention claimed in claim 3, the partial breakage by the contact of the opposed ends of the first and second tubular bodies assures a further simplified and positive releasing operation, while assuring a cost reduction by a reduction in part number as well as a simplification of the construction.

In an operational effect of the invention claimed in claim 4, a piercing of the needle part of the second container to the plug of the first container together with a relative slide movement between the first and second tubular bodies until a mutual contact of the respective opposed ends assures that the first tubular body facing the second tubular body is at least partially broken, resulting in the release of the sealed condition of the second medicine in the first tubular body, so that the second medicine is transported into the first container via the needle shaped part pierced to the plug of the first container. As a result, a positive co-infusion of the second medicine into the first medicine is obtained. Furthermore, the release of the sealed condition by the partial breakage assures a cost reduction thanks to the reduction in part number as well as a simplified structure.

In an operational effect of the invention claimed in claim 5, a release of the sealed condition of the second medicine by the relative movement of between the first and second tubular bodies is done after the completion of the piercing of the needle part to the plug of the first container, which eliminates any possibility of leakage of the second medicine during the execution of the co-infusion operation.

In an operational effect of the invention claimed in claim 6, the broken part is constructed by the lug toward the opposed wall, to which a bending force is applied in a manner that the lug is broken at its root portion, thereby assuring a reliable release operation.

In an operational effect of the invention claimed in claim 7, the lug of integrated structure makes its molding process to be simplified, on one hand and, on the other hand, the release of the sealed condition to be reliable due to the fact that the lug is able to be positively broken.

In an operational effect of the invention claimed in claim 8, the lug after the completion of the breakage is stored in the recessed portion, so that an increased co-infusion efficiency is obtained, on one hand and, on the other hand, the broken part is prevented from being floated in the inside space.

In an operational effect of the invention claimed in claim 9, the provision of the positioning means makes it possible that the lug and the recess are reliably engaged when a release of the sealed condition is done.

In an operational effect of the invention claimed in claim 10, the provision of the means for confirming the release of the sealed condition by the breakage assures that a co-infusion operation is reliably practiced even when an operator is untrained. Such a confirmation means is constructed by any suitable means including auditory means such as clicking means and visual means including an identification mark or characters et al.

In an operational effect of the invention claimed in claim 11, a piercing of the needle part of the second container to the plug of the first container followed by a relative slide movement between the first and second tubular bodies assures that that a release of the sealed condition of the second medicine and a subsequent transportation of to the first container are obtained for obtaining a simplified and a reliable mixing operation with the first medicine.

In an operational effect of the invention claimed in claim 12, a release of the sealed condition of the second container is surely occurred after the completion of the piercing to the plug of the first container, so that a positive transportation of the second medicine in the second container is obtained, while preventing any leakage from being occurred.

BRIEF EXPLANATION OF ATTACHED DRAWINGS

EXPLANATION OF REFERENCE NUMERALS

10 Port Body
11 Needle Body
12 Central Flow Channel of Port Body
20 Breakable Lug
30 Positioning Rib
40 Central Flow Channel of Needle Body
42 Needle Part
46 Side Hole
50 Recess For Reception of Breakable Lug
60 U-Shaped Guide
62 Guide Groove
80 Soft Container
84 Space for Storing Medicine of Soft Container
90 Infusion Bag
94 Space of Infusion Bag
96 Port Member of Infusion Bag

BEST MODE FOR PRACTICING THE INVENTION

Figure 1:
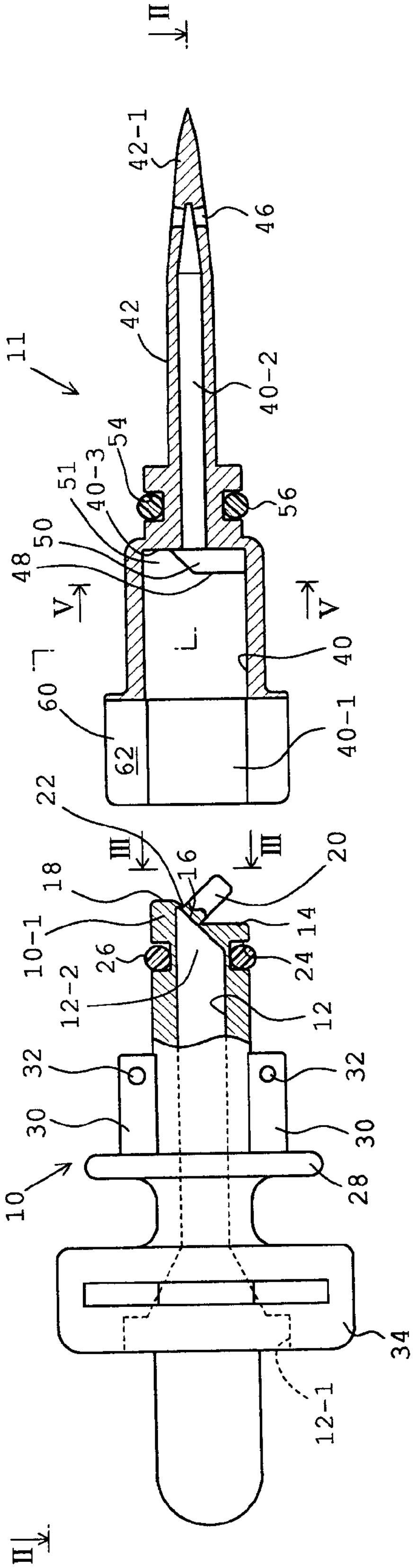
FIG. 1 is a partially sectional plan view of a port body and needle body prior to their assembly, viewed along lines I-I in FIG. 2.
Figure 2:
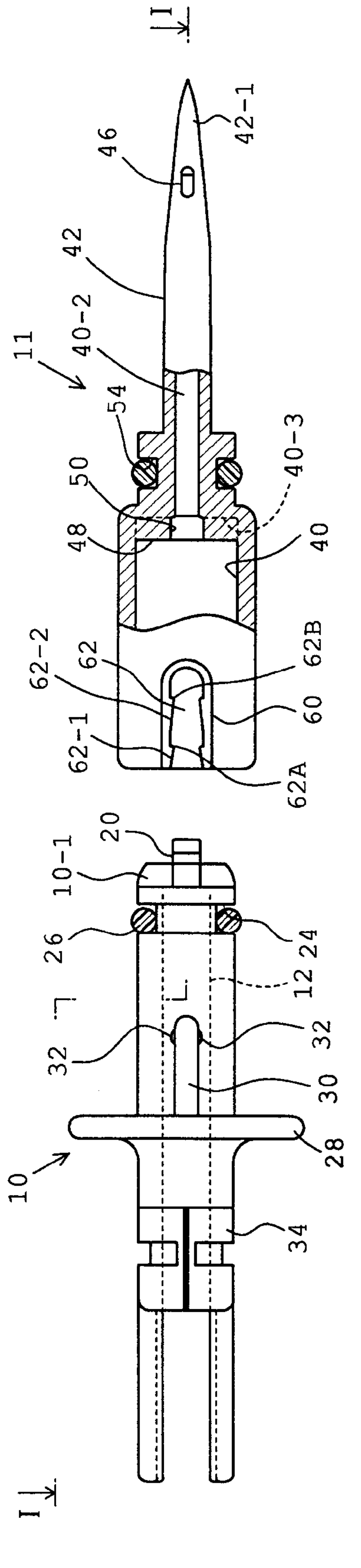
FIG. 2 is similar to FIG. 1 but illustrates a partially sectional side view, taken along line II-II in FIG. 1.

Now, a first embodiment of the present invention will be explained, which is directed to a medical injection device for injecting (co-infusing), into an infusion bag (first medical storage) for storing therein with a medicine(s) such as a glucose and physiological saline solution et al (first medicine(s)), a different medicine(s) such as a vitamin(s) (second medicine(s)). In FIGS. 1 and 2, medical injection device includes a port body 10 (a first body or a first cylindrical body of the invention) and a needle body 11 (a second body or a second cylindrical body of the invention). As will be explained later, the port body 10 is connected to a soft container (second container) made of plastic films for storing therein with a second or additional medicine(s) for a co-infusion. As also be explained later, the needle body 11 has a needle portion, which is pierced to a rubber plug of an infusion bag, so that the medicine stored in the plastic soft container is introduced (co-infused) into the infusion bag.

In FIGS. 1 and 2, the port body 10 is preferably made of a plastic material, which has rigidity high enough to make the port body to maintain its shape and which includes, although non-exclusively, ABS (acrylonitrile-styrene-butadien co-polymer) resin, PP (polypropylene) resin, PE (polyethylene) resin, rigid PVC (polyvinyl chloride) resin, PC (polycarbonate) resin, COP (cycloolefin) resin, PS (polystyrene) resin, acrylate resin or PET (polyethylene terephthalate) resin, et al. The port body 10 forms, generally, a cylindrical shape and has a central flow channel 12, which extends in the axial direction. The central flow channel 12 has an opened first end 12-1 remote from the needle body 11, which is more or less widened and has a closed second end 12-2 located adjacent the needle body 11. At the end faced with the needle body 11, the port body 10 forms a vertical wall 14 located below the horizontal diametric line, an inclined wall 16 of relatively thin thickness located above the horizontal diametric line, providing an axially projected part 10-1 and an uppermost vertical wall 18 as an extension from the inclined wall 16 (See also FIG. 3). In short, the portions 14, 16 and 18 construct an end wall of the port body 10 faced with the needle body 11, which extends along the entire area of the end of the central flow channel 12 adjacent the needle body 11. In other words, the central flow channel 12 is usually closed at the end adjacent the needle body 11.

Figure 3:
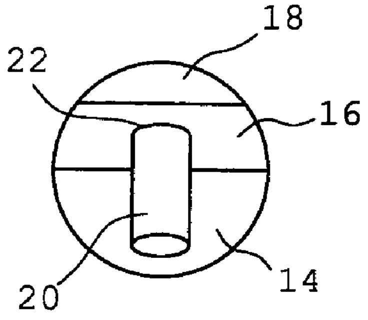
FIG. 3 is an end view of the port body at a portion spaced from the side where a soft container is to be located, taken along lines III-III in FIG. 1.
Figure 4:
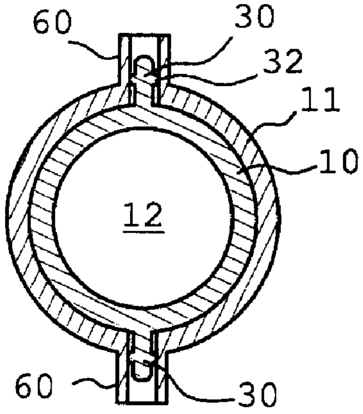
FIG. 4 is a transverse cross-sectional view of the fitted part between the port body and the needle body, taken along lines IV-IV in FIG. 6.

As shown in FIG. 3, the inclined wall 16 is integrally formed with a lug 20 of a rod shape. Due to the inclination of the wall 16, the lug 20 is directed downward with respect to the axis of the port body 10 as shown in FIG. 1 and extends across the vertical wall portion 18, which is the end of the port body 10 adjacent the needle body 11. When the port body 10 is inserted into the needle body 11 as will be fully explained later, the lug 20 is initially engaged with the opposed surface of the needle body 11, which causes the lug 20 to be bent downward in FIG. 1. The inclined wall 16, from which the lug 20 is extended, is thin walled at the root end of the lug 20 and forms a weak or breakable part 22. An engagement of the lug 20 with the opposed surface of the needle body 11 causes the lug 20 to be forced downward, so that the lug 20 is finally broken at the weak part 22 at least at the stretched side, so that the seal or closure of the port body 10 at the end adjacent the needle body is released, which causes the central flow channel 12 to be opened to the needle body 11. Such a thin walled portion 22 in the inclined wall 16 is formed at the entire or partial periphery of the breakable lug 20. Furthermore, the lug 20 may be hollowed, so that a thin walled structure is obtained along its entire or partial peripheral wall. Furthermore, in order to obtain an easily breakable structure, the lug 20 may advantageously be formed with an U-shaped notch(s) functioning as a thin walled portion according to the present invention.

The port body 10 is formed with an annular groove 24 along its outer periphery, to which annular groove 24 O-ring 26 is fitted, which O-ring is for obtaining a sealing function of the inserted portion between the port body 10 and the needle body 11. Furthermore, the port body 10 is, at its diametric opposed locations of its outer periphery, formed with positioning ribs 30 (positioning means according to the present invention), each of which ribs extends along the longitudinal direction from an ring shaped flange portion 28 to a location adjacent the annular groove 24. As will be explained later, when the port body 10 is inserted to the needle body 11, these ribs 30 are fitted to respective positioning grooves of the needle body 11, so that a relative positioning between the parts 10 and 11 is positively obtained in a circumferential direction, thereby preventing the parts 10 and 11 from relatively rotating. Finally, the rib 30 is, at its opposed side surfaces, integrally formed with semispherical shaped projections 32 for obtaining locking function.

Furthermore, the port body 10 is formed with a flattened flange portion 34 at a location on the side of the open end 12-1 of the central flow channel 12. As will be explained later, plastic films constructing a soft container for storing a medicine(s) for a co-infusion are thermally bonded to the flange portion 34 under a liquid sealed manner.

Now, a construction of the needle body 11 will be explained. The needle body 11 is, as similar to the port body 10, formed as a cylindrical shape and is preferably made of a plastic material, which is rigid enough for needle body 11 to maintain its shape and which include, although non-exclusively, ABS (acrylonitrile-styrene-butadien co-polymer) resin, PP (polypropylene) resin, PE (polyethylene) resin, rigid PVC (polyvinyl chloride) resin, PC (polycarbonate) resin, COP (cycloolefin) resin, PS (polystyrene) resin, acrylate resin or PET (polyethylene terephthalate) resin, et al. The needle body 11 is generally formed as a cylindrical shape and has a central flow channel 40 extending axially. The channel 40 has a first, straight open end 40-1, to which the leading end of the port body 10 is inserted as will be explained later and a second end 40-2 extending to a needle part 42 of the needle body 11. The central flow channel 40 has a reduced inner diameter at the needle part 42. The needle body 11 has side holes 46 opened outside at locations slightly upstream from a pointed end 42-1 of the needle part 42. During a co-infusion process, a medicine from the co-infusion container is transported to an infusion bag via the side holes 46 as will be described later.

Figure 5:
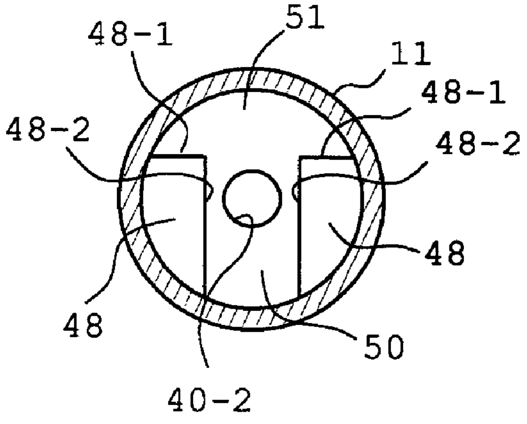
FIG. 5 is a transverse cross-sectional view of the needle body, taken along lines V-V in FIG. 1.

The straight portion of the central flow channel 40 has an inner bottom 40-3, which is formed with a pair of raised lands 48 (FIG. 5) astride the longitudinal axis of the central flow channel 40. These lands 48 terminate at edges 48-1 and 48-2 crossing at angle of 90 degree, so that a groove or recess 50 extending along the diametric direction is formed between the opposed edges 48-2 and a crescent shaped recess 51 is formed on one side of the inline edges 48-1 away from the lands 48. The groove 50 has a width, which is more or less larger than the diameter of the lug 20 of the port body 10. When an insertion of the port body 10 into the needle body 11 is commenced for the co-infusion operation, the lug 20 is reliably received by the groove 50. In the situation that the insertion of the port body 10 into the needle body is completed and the lug 20 is broken at the weak portion 22, the lug 20 is completely stored and held in the groove 50, resulting in a reduction of a dead space volume, on one hand and, on the other hand, a waste-less transportation of the medicine in the co-infusion container into the infusion bag.

Figure 6:
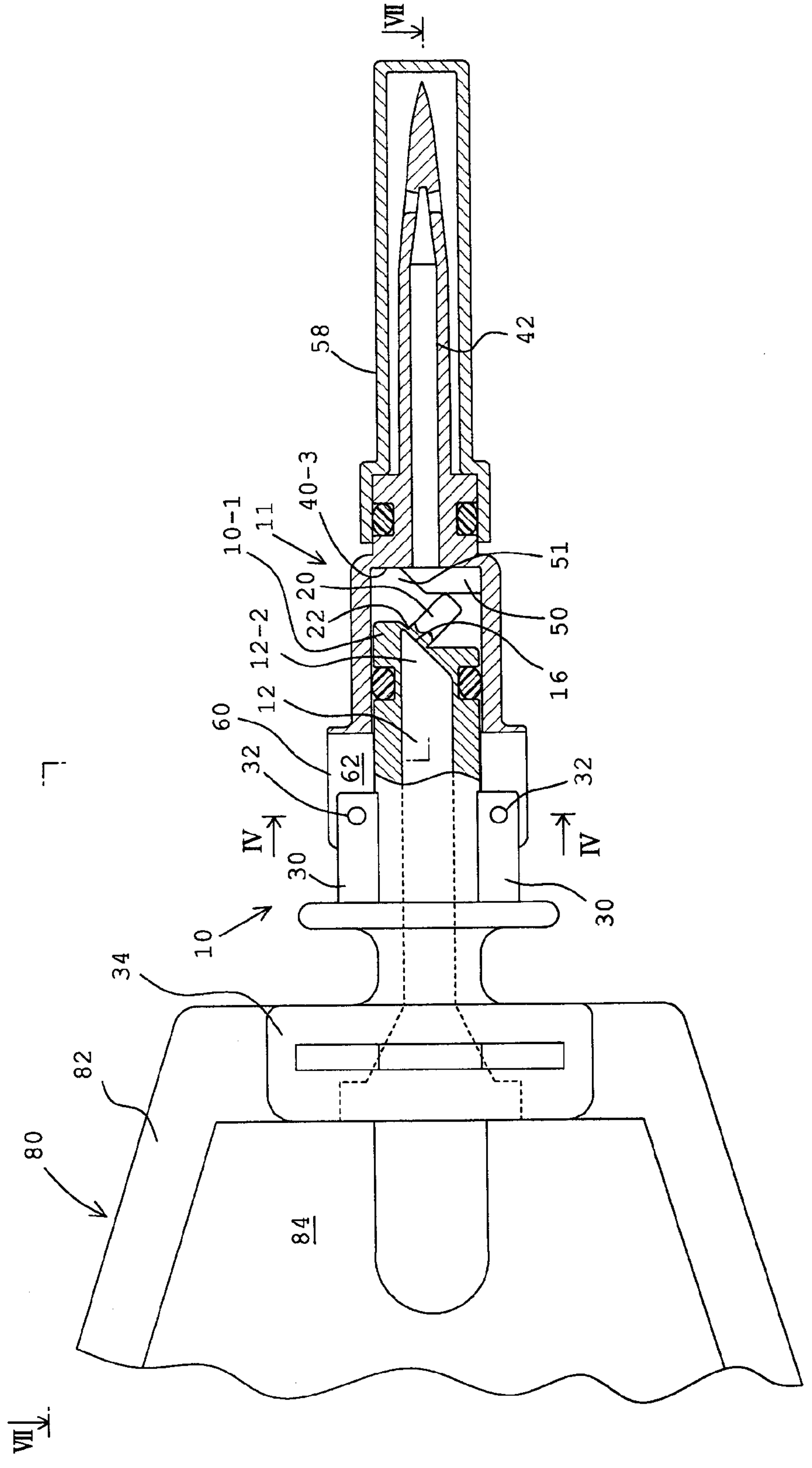
FIG. 6 is a partially sectional plan view of a co-infusion assembly under an assembled but non-released condition, taken along lines VI-VI in FIG. 7.

As shown in FIG. 1, the needle body 11 is, on its outer surface, formed with an annular groove 54 at a location adjacent the needle 42. An O-ring 56 is fitted to the annular groove 54 for obtaining a seal function with respect to a needle protection cap 58 as shown in FIG. 6. Furthermore, the needle body 11 is integrally formed with a pair of U-shaped guides 60 at diametrically opposed positions adjacent the open end of the needle body 11 away from the needle 42-1. As shown in FIG. 2, each of the guides 60 is formed as a U-shaped cross-section and is provided with an inner guide groove 62 opened to the port body 10. Thus, the guide ribs 30 of the port body 10 are capable of being inserted to the respective guide grooves 62. As shown in FIG. 2, each of the guide grooves 62 is provided with a pair of opposed inner walls, each of which is formed with a series of stepped tapered surfaces 62-1 and 62-2 and locking notches 62A and 62B at the ends of tapered surfaces 62-1 and 62-2, respectively. As will be described later, the locking projections 32 of the guide ribs 30 on the port body 10 are selectively engaged with these locking notches 62A and 62B, so that a locking or detent of two stepped varied depth of the port body 10 with respect to the needle body 11 is obtained between a sealed condition, where the device is assembled but not released and a fully push-in condition, where the device is released and a co-infusion process is done.

The O-rings 26 and 56 are made from an elastic material although not limitative, which includes a rubber, such as silicon rubber, butyle rubber, isoprene rubber or natural rubber or a high-molecular elastomer, such as styrene based elastomer, olefin based elastomer, polyester based elaster or nylon based elastomer.

Figure 7:
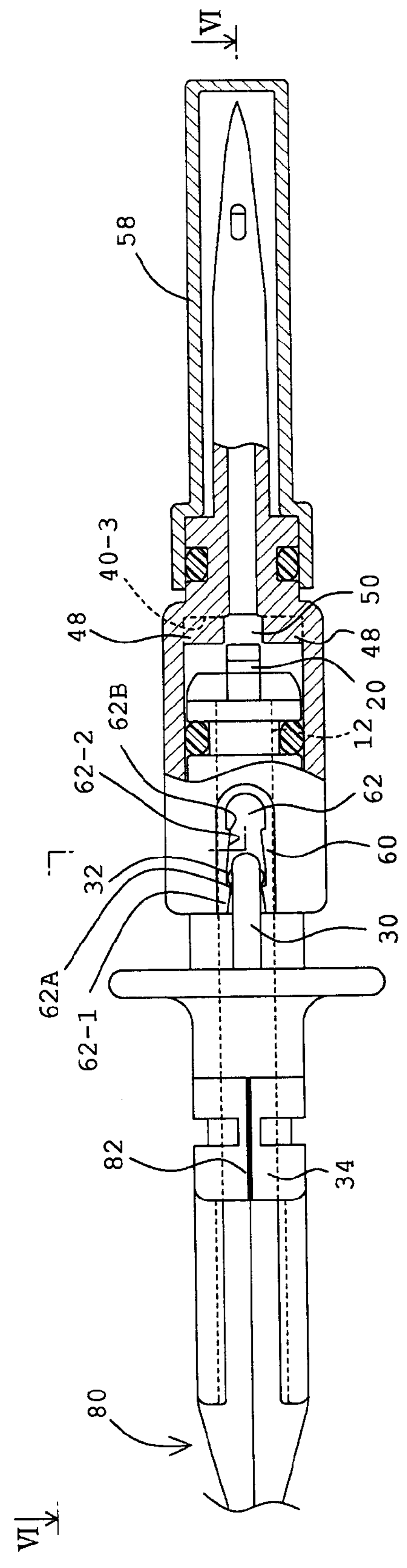
FIG. 7 is a partially sectional plan view of a co-infusion assembly under an assembled but released condition, taken along lines VII-VII in FIG. 6.

Now, a manner of use of the medical transportation device of the present invention will be explained, when applied for a co-infusion process to an infusion bag. FIGS. 6 and 7 illustrate an assembled condition of the port body 10 and the needle body 11, wherein the port body 10 is, from its closed end, inserted to the open end 40-1 at the rear end of the needle body 11. Prior to the insertion, a positioning is done in a rotating direction between the port body 10 and the needle body 11 in a manner that the ribs 30 on the port body 10 is aligned with guide grooves 62 on the needle body 11 and that the projected part 10-1 of the port body 10 is opposed with the recess 51 of the needle body 11. When such a positioning is obtained, the port body 10 is pushed into the needle body 11, which causes the positioning ribs 30 to be guided and inserted into the respective guide grooves 62. By a further insertion of the port body 10 into the needle body 11, the lock projections 32 on the positioning ribs 30 move on the first tapered surfaces 62-1 of the respective guide groove 62, so that a condition as shown in FIG. 7 is finally obtained, where the lock projection 32 climbs over the first tapered surface 62-1. At this condition, the lock projection 32 of the positioning rib 30 engages with the lock notch (recessed portion) 62A at a leading end of the second tapered surface 62-2. As a result, the port body 10 and the needle body 11 are locked at the relative axial position (an assembled but non-released state) as shown in FIGS. 6 and 7 against some degree of a resilient force. In this assembled position, the weak, lug 20 at the leading end of the port body 10 is, as shown in FIG. 6, faced with the groove 50 between the lands 48 and spaced from the faced bottom wall 40-3 of the cylindrical bore of the needle body 11, so that the lug 20 maintains the integrated condition with respect to the remaining part of the port body, i.e., the thin walled inclined wall 16 (FIG. 3). Thus, the central flow channel 12 of the port body 12 maintains the closed or non-released condition at the end 12-2 adjacent the needle body 11. Finally, a needle cap 58 is attached.

Figure 10A:
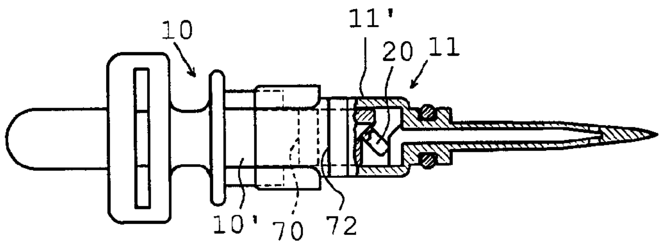
FIG. 10 is a partially sectional plan view of a co-infusion container provided with a means for confirming a released condition based on an alignment of transparent parts, wherein (a) illustrates a non-released condition and (b) a released condition.
Figure 10B:
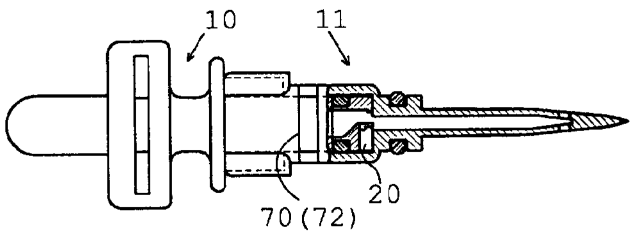
Figure 11A:
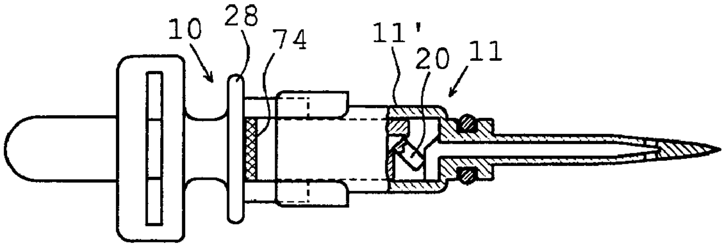
FIG. 11 is a partially sectional plan view of a co-infusion container provided with a means for confirming a released condition based on a closure of indexing part, wherein (a) illustrates a non-released condition and (b) a released condition.
Figure 11B:
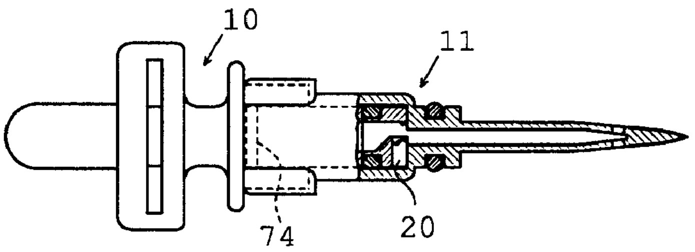

In the assembled condition between the port body 10 and the needle body as shown in FIGS. 10 and 11, a formation of a soft container for co-infusion as well as a sealed introduction of a medicine are done. Namely, a pair of plastic resin films is superimposed and their opposed outer peripheral portions are subjected to a thermally bonding process, so as to obtain a bag (soft container). Such a soft container is shown partly by a reference numeral 80 in FIG. 6 and has a sealed part 82 (thermally bonded part of the plastic films) along the outer periphery of the container. However, the soft container 80 is partly non-sealed at a location along the outer periphery, so that an opening is formed. To the opening, the flattened flange portion 34 of the port body 10 is inserted and the plastic films at the opening of the soft container 80 are, then, welded to the opposed outer surface of the flattened flange 34. Then, a medicine(s) is introduced into a space 84 inside the soft container 80, which is sealed in a well-known manner. Thus, a co-infusion container assembly as shown in FIG. 6 is obtained, which assembly is constructed by an injector part constructed by the port body 10, to which the needle part 11 is fitted, with the needle 42 covered by the needle cap 58 and the soft container 80 connected to the injector part.

Figure 8:
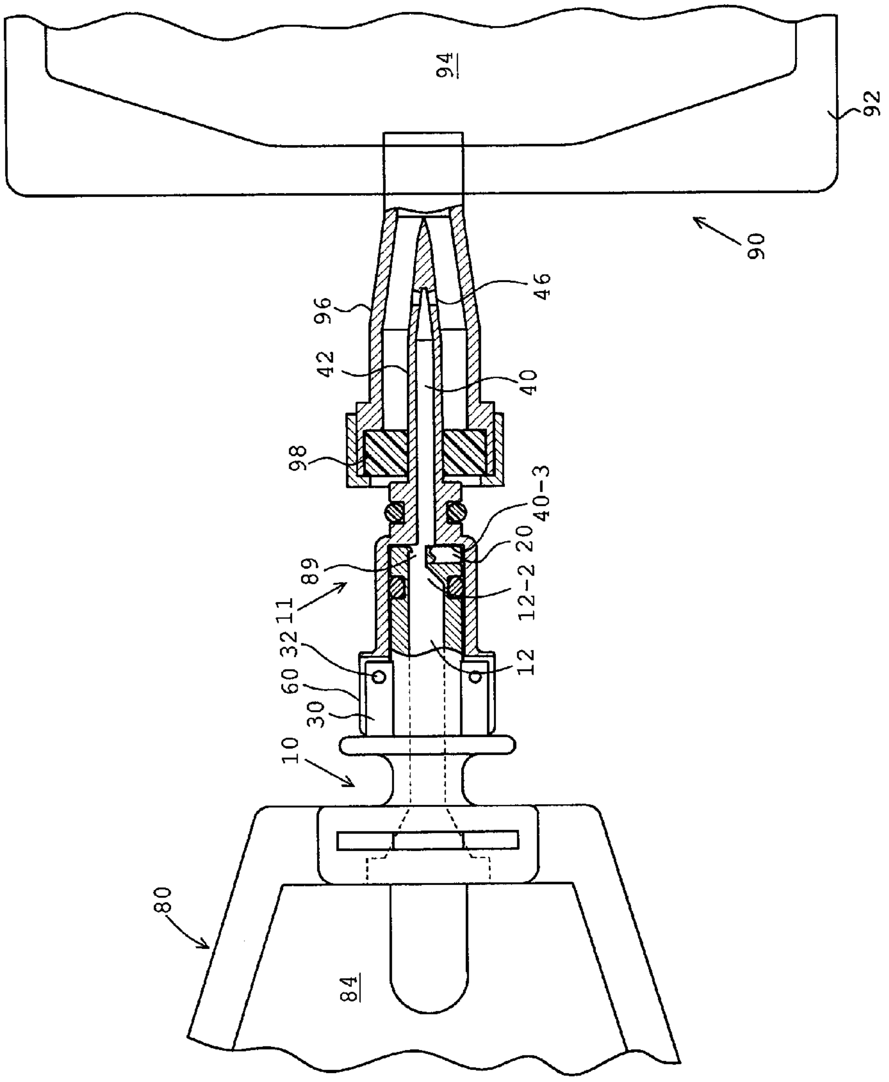
FIG. 8 is a partially sectional plan view of a co-infusion assembly during an execution of co-infusion operation.

Next, a co-infusion operation to an infusion bag, using the container assembly shown in FIGS. 6 and 7 will be explained. As illustrated in FIG. 8, such an infusion bag 90 (soft container) may, in a well known manner, be constructed by a pair of superimposed, plastic films, which are thermally bonded for forming a bag having a thermally bonded outer peripheral part 92, having an inner space 94 for storing a medicine(s) for an infusion, such as glucose liquid and/or physiological saline solution and by an inlet port 96 at an upper end of the thermally bonded outer peripheral part 92. The inlet port 96 is a molded article of a cylindrical shape from a suitable plastic resin material. The inlet port 96 is, at its outer end, provided with a plug 98 made of a resilient material, such as a rubber. In order to transport (co-infuse) the medicine in the soft container 80 into the infusion bag 90, the co-infusion assembly is entirely pushed toward the infusion bag 90 in a manner that the needle 42 of the assembly pierces the rubber plug 98 of the bag 90. A force needed for obtaining a slide movement between the port body 10 and the needle body 11 (slide resistance) is made larger than a force needed for piercing the rubber plug 98 with the needle 42 (piercing resistance) by suitable adjustments of various factors, such as a degree of fitting between the port body 10 and the needle body 11, a shape of the needle and a type of surface working, et al. As a result, a relative position between the port body 10 and the needle body 11 as shown in FIG. 6, i.e., the position of the lug 20 spaced from the opposed surface 40-3, is maintained until the needle 42 is pierced fully to the rubber plug 98 as shown in FIG. 8. As a result, the closed or non-released state of the end 12-2 of the central flow channel 12, i.e., the sealed state of the medicine in the soft container 84 is maintained. As a result, the medicine in the soft container 80 is prevented from being issued or leaked from the assembly.

In order to commence a co-infusion operation, under a condition that the needle 42 is completely pierced to the rubber plug 98 as shown in FIG. 8, the co-infusion bag assembly is further pushed along a direction toward the medical bag 90, which finally causes the port body 10 to be displaced against the slide resistance with respect to the needle body 11, so that a relative slide movement of the port body 10 with respect to the needle body 11 is commenced. During such a slide movement, the lug 20 at the tip end of the port body 10 is firstly guided into the groove 50 between the lands 48 (FIG. 5) and is secondly contacted with the opposed surface 40-3, so that the lug 20 is subjected to a bending force directed downwardly in FIG. 6 due to the downwardly directed inclination, resulting in a breakage of the lug 20 at the weak, thin wall portion at the root 22. Such an opening or release by the breakage of the lug 20 may occur at the bending side, i.e., the lug 20 may still be connected at the opposite side. FIG. 8 shows a fully pushed-in condition that the port body 10 and needle body 11 are contacted with each other at their faced ends, where the lug 20 is under an upright position and is stored in the groove 50 between the lands 48. In this fully pushed-in condition as shown by FIG. 8, the locking projections 32 climb over the second taper surfaces 62-2 of the guide groove 62 and are engaged with the respective notches 62B, so that the relative position between the port body 10 and needle body 11 as shown in FIG. 8, i.e., the opened state of the assembly is maintained under a resilient force. As a result of the breakage of the lug 20 as shown in FIG. 8, the sealed condition at the inclined surface 16 (FIG. 3) is broken or released, resulting in a creation of an opening 89 (FIG. 8), through which the central flow channel 12 of the port body 10 is made communication with the central flow channels 40 and 40-2 of the needle body 11. As a result, the medicine stored in the soft container 80 is introduced into the central flow channels 12, 12-2, 40 and 40-2 and is, via the side holes 46, transported into the space 94 inside the infusion bag 90.

In the above embodiment, when the push-in operation is done until the rapture of the lug 20, the locking projection 32 climb over to the second notches 62B shown in FIG. 7, which causes a click to be generated, which functions as an auditory notification to an operator that the push-in operation for obtaining an opened condition (a release of the sealed condition) of the device is completed. Additionally or alternatively, a visual means may be provided for notifying a desired push-in depth as obtained even to any untrained operator, thereby preventing an erroneous operation from being occurred. Namely, in the instant embodiment, when a push-in operation is done so that the lug 20 is broken, a gap between the annular flange 28 on the port body 10 and guide rib 30 on the needle body 11 is just cancelled. Thus, a zero value of such gap becomes a verification or notification that a desired degree of the push-in operation is obtained.

Figure 9A:
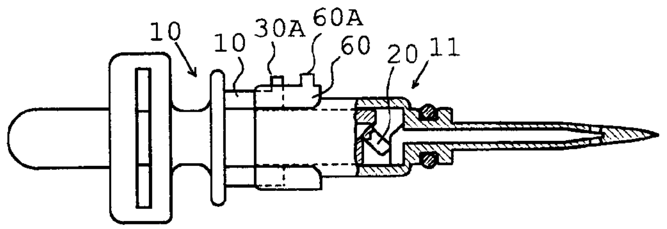
FIG. 9 is a partially sectional plan view of a co-infusion container provided with a means for confirming a released condition based on an alignment of projected parts, wherein (a) illustrates a non-released condition and (b) a released condition.
Figure 9B:
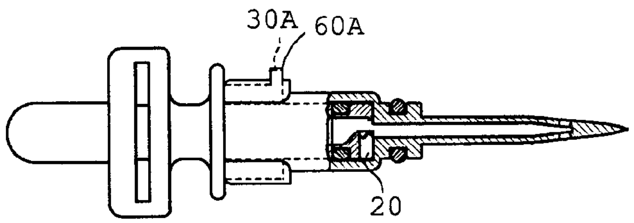

FIG. 9 illustrates a modification of confirmation means of the completion of a push-in operation. Namely, in this embodiment, the guide rib 30 of the port body 10 is formed with a projected portion 30A and the U-shaped guide 60 of the needle body 11 is formed with a projected portion 60A. At the usual, non-opened condition, where the lug 20 is un-broken as shown in FIG. 9(*a*), the projected portions 30A and 60A are separated from each other. At the opened condition, where the lug 20 is broken as shown in FIG. 9(*b*), the projected portions 30A and 60A are aligned, so that the push-in depth between the port body 10 and needle body 11 for obtaining the opening is easily and positively affirmed.

FIG. 10 illustrates a modification of means for a confirmation of the completion of a push-in operation, including a transparent type alignment system. Namely, the port body 10 has, at its tubular part 10' inserted to the needle body 11, a circumferentially extending transparent band 70. On the other hand, the needle body 11 has, at its tubular part 11' to which the tubular part 10' of the port body 10 is inserted, a circumferentially extending transparent band 72. The port body 10 and the needle body 11 are made opaque by printing or label adhesion or embossing (surface roughing) et al at locations other than those where the transparent band 70 and 72 are located. In a usual non-opened condition, where the lug 20 is unbroken as shown in FIG. 10(*a*), the transparent band 70 and 72 are axially spaced and not overlapped, thereby preventing from being entirely see-through. In an opened condition, where the lug 20 is broken as shown in FIG. 10(*b*), the transparent band 70 and 72 are overlapped and thus entirely see-through, which becomes a notification of a completion of a desired depth of push-in operation.

In the embodiment of FIG. 10, a modification is possible, wherein a suitable letter, such as "RELEASE" or "OPEN", is printed on the band shaped area 70 of the port body 10, which is now not necessarily be transparent. In a usual non-opened condition, where the lug 20 is unbroken as shown in FIG. 10(*a*), the transparent band 70 and 72 are axially spaced and not overlapped, so that the band 70 is covered by the non-transparent part of the needle body 11 located on the upper side, which prevents the letter of "RELEASE" or "OPEN" from being seen. In an opened condition, where the lug 20 is broken as shown in FIG. 10(*b*), the transparent band 70 and 72 are overlapped, so that the letter of "RELEASE" or "OPEN" printed on the band area 70 of the port body 10 located on the lower side is seen through the transparent band area 72 of the needle body 11 located on the upper side, which functions as a notification of a completion of a desired depth of push-in operation.

FIG. 11 shows a different embodiment of a confirmation means of a push-in depth, where an identification part 74 is provided on the port body 10, which part is closed during the opened condition. Namely, the identifying part 74 is a letter, such as "NON-RELEASE" or "CLOSE" or a mark or line et al and is arranged at the location adjacent the flange 28. In a usual non-opened condition, where the lug 20 is unbroken as shown in FIG. 11(*a*), the flange 28 is spaced from the end of the needle body 11, so that the identification part 74 is outwardly exposed, causing an operator to notice the indication of "NON-RELEASE" or "CLOSE". In an opened condition, where the lug 20 is broken as shown in FIG. 11(*b*), the indication such as "NON-RELEASE" or "CLOSE" is covered by the needle body 11, which is opaque, which prevents the letter or line from being visually noticed, which functions as a notification of a completion of a desired depth of push-in operation.

Figure 12A:
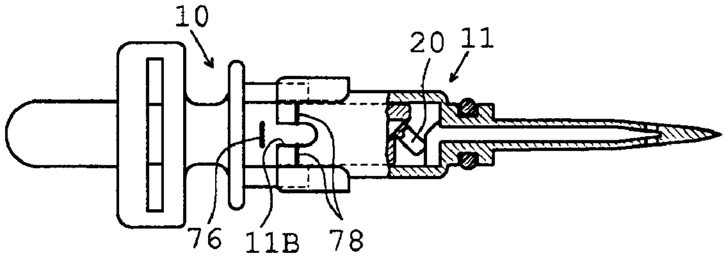
FIG. 12 is a partially sectional plan view of a co-infusion container provided with a means for confirming a released condition based on a coincidence of index marks, wherein (a) illustrates a non-released condition and (b) a released condition.
Figure 12B:
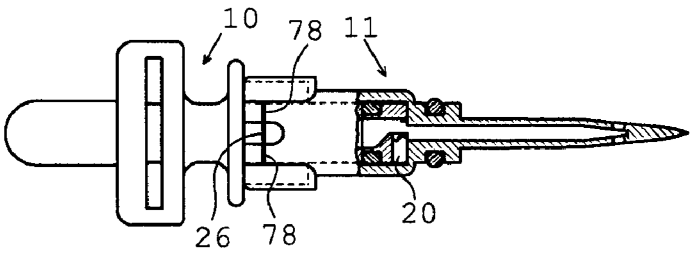

FIG. 12 shows a different embodiment of a confirmation means of a push-in depth for a confirmation by a coincidence of lines. Namely, on the outer periphery of the port body 10, a first judging mark 76 of line shape is printed. On the needle body 11, a second judging line 78 astride a groove 11B is printed at the end of the body 11. In a usual non-opened condition, where the lug 20 is unbroken as shown in FIG. 12(*a*), the lines 76 and 78 are spaced, so that a judgment of un-opened condition is obtained. In an opened condition, where the lug 20 is broken as shown in FIG. 12(*b*), the lines 76 and 78 are coincided, so that a judgment of opened condition is obtained.

The invention claimed is:

1. A device for transporting a fluid from a first storage bag to a second storage bag, the device comprising:

a first body having for receiving the fluid from the first storage bag; and a second body for receiving the fluid from the first body and dispensing the fluid into the second storage bag;

wherein:

the first body comprises an axial passage through which the fluid may pass, a first end capable of attachment to the first bag, and a second end removably attached to the second body;

the second body comprises an axial passage through which the fluid may pass, a first end capable of attachment to the second bag, and a second end removably attached to the first body;

the first body and the second body are capable of being moved in an axial direction with respect to one another;

the second end of the first body comprises a breakable seal that prevents the fluid from passing from the first body to the second body;

the breakable seal comprises an inclined wall and a lug projecting from the inclined wall;

the inclined wall is inclined with respect to the axial passage of the first body;

the breakable seal is broken when the first body and the second body are moved toward one another in the axial direction; and the breakable seal breaks by being displaced away from the first body.

2. The device of claim 1, wherein the breakable seal is broken when a surface of the second body presses against the lug and pulls at least a portion of the inclined wall away from a remainder of the first body.

3. The device of claim 2, wherein, after the breakable seal is broken, the lug is held between a portion of the first body and a portion of the second body.

4. The device of claim 1, wherein the first end of the second body comprises a needle for insertion into the second storage bag.

5. The device of claim 4, wherein a value of slide resistance force between the first body and the second body when the first body and the second body are moved with respect to one another in an axial direction is greater than a force required to pierce a plug of the second storage bag with the needle of the second body.

6. The device of claim 1, further comprising means for relative rotational positioning between the first body and the second body when the first body and the second body are moved with respect to one another in an axial direction.

7. The device of claim 1, further comprising means for confirming completion of relative movement between the first body and the second body to cause breakage of the breakable seal, when the first body and the second body are moved with respect to one another in an axial direction.

8. A storage bag for co-infusion of a fluid, comprising the device of claim 1, wherein the device is connected to and in communication with the first storage bag.

9. A device for transporting a fluid from a first storage bag to a second storage bag, the device comprising:

a first body having for receiving the fluid from the first storage bag; and a second body for receiving the fluid from the first body and dispensing the fluid into the second storage bag;

wherein:

the first body comprises an axial passage through which the fluid may pass, a first end capable of attachment to the first bag, and a second end removably attached to the second body;

the second body comprises an axial passage through which the fluid may pass, a first end capable of attachment to the second bag, and a second end removably attached to the first body;

the first body and the second body are capable of being moved in an axial direction with respect to one another;

the second end of the first body comprises a breakable seal that prevents the fluid from passing from the first body to the second body;

the breakable seal comprises an inclined wall and a lug projecting from the inclined wall;

the inclined wall is inclined with respect to the axial passage of the first body; and the breakable seal is broken when the first body and the second body are moved toward one another in the axial direction, and the broken seal is prevented from moving along the axial passages of the first body and the second body.

10. The device of claim 9, wherein the breakable seal is broken when a surface of the second body presses against the lug and pulls at least a portion of the inclined wall away from a remainder of the first body.

11. The device of claim 10, wherein, after the breakable seal is broken, the lug is held between a portion of the first body and a portion of the second body.

12. The device of claim 9, wherein the first end of the second body comprises a needle for insertion into the second storage bag.

13. The device of claim 12, wherein a value of slide resistance force between the first body and the second body when the first body and the second body are moved with respect to one another in an axial direction is greater than a force required to pierce a plug of the second storage bag with the needle of the second body.

14. The device of claim 9, further comprising means for relative rotational positioning between the first body and the second body when the first body and the second body are moved with respect to one another in an axial direction.

15. The device of claim 9, further comprising means for confirming completion of relative movement between the first body and the second body to cause breakage of the breakable seal, when the first body and the second body are moved with respect to one another in an axial direction.

16. A storage bag for co-infusion of a fluid, comprising the device of claim 9, wherein the device is connected to and in communication with the first storage bag.

* * * * *